United States Patent [19]

Bunno et al.

[11] Patent Number: 4,867,914

[45] Date of Patent: Sep. 19, 1989

[54] PREGNANE DERIVATIVES AND METHOD OF PRODUCING THE SAME

[75] Inventors: Masayasu Bunno, Chiba; Hidemi Harada, Kurashiki; Masao Tsuji, Kurashiki; Yoshihiro Ichihara, Kurashiki, all of Japan

[73] Assignee: Kuraray Co., Ltd., Kurashiki, Japan

[21] Appl. No.: 911,970

[22] Filed: Sep. 26, 1986

Related U.S. Application Data

[63] Continuation of Ser. No. 806,440, Dec. 9, 1985, abandoned, which is a continuation of Ser. No. 701,973, Feb. 15, 1985, abandoned, which is a continuation of Ser. No. 469,743, Feb. 25, 1983, abandoned.

[30] Foreign Application Priority Data

Feb. 26, 1982 [JP] Japan .................................. 57-30899
May 21, 1982 [JP] Japan .................................. 57-87047
Jun. 21, 1982 [JP] Japan .................................. 57-107448

[51] Int. Cl.$^4$ ................................................. C07J 1/00
[52] U.S. Cl. ................................................. 260/397.47
[58] Field of Search ..................................... 260/397.47

[56] References Cited

FOREIGN PATENT DOCUMENTS

0152498  11/1981  Japan .................................. 260/397.3

Primary Examiner—Douglas W. Robinson
Assistant Examiner—Joseph A. Lipovsky
Attorney, Agent, or Firm—Burns, Doane, Swecker & Mathis

[57] ABSTRACT

There are provided 12-hydroxy-$\Delta^4$ or $\Delta^{1,4}$-pregnan-3-one-20-carbaldehyde and microbial method of producing the same. The compounds are novel and useful as starting materials for the synthesis of corticoids, typically prednisone, prednisolone and hydrocortisone, which have antiinflammatory activity.

4 Claims, No Drawings

PREGNANE DERIVATIVES AND METHOD OF PRODUCING THE SAME

This application is a continuation of Ser. No. 806,440, filed Dec. 9, 1985, now abandoned, which is a continuation of Ser. No. 701,973, filed Feb. 15, 1985, now abandoned, which is a continuation of Ser. No. 469,743, filed Feb. 25, 1983, now abandoned.

BACKGROUND OF THE INVENTION

1. Field of the Invention

This invention relates to pregnane derivatives of the general formula

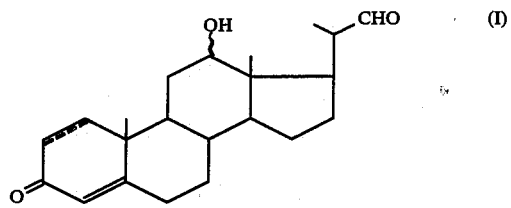

wherein the dotted line --- represents the possibility of there being a double bond and wavy line indicates that the hydroxyl group is either in the α- or in the β-configuration, and a method of producing the same with the aid of a microbe.

2. Description of the Prior Arts

The pregnane derivatives of the general formula (I) as provided by the present invention are novel compounds not yet described in the literature buy obtainable by allowing a specific microbe to act upon deoxycholic acid and/or a salt thereof. These compounds can be used as starting materials for the synthesis of excellent antiinflammatory corticoids represented by prednisone, prednisolone, hydrocortisone, etc..

The so-far known process for producing prednisone starts with deoxycholic acid and involves twenty-odd steps [L. F. Fieser and M. Fieser: Steroids, pages 634–647, Reinhold, 1959]. However, as the reagents required are expensive and the process is time-consuming, the process is not fully satisfactory for industrial application.

An object of the present invention is to provide novel pregnane derivatives which are useful as starting materials for the synthesis of various corticoids.

Another object of the present invention is to provide novel pregnane derivatives which are useful as advantageous starting materials for the synthesis of prednisone, prednisolone and hydrocortisone.

A further object of the present invention is to provide a method of producing the above-mentioned novel and useful pregnane derivatives.

These objects as well as other objects and advantages of the present invention will become apparent to those skilled in the art from the following detailed description.

SUMMARY OF THE INVENTION

The present invention provides the novel pregnane derivatives of the general formula (I) shown above.

The present invention also provides a method of producing the pregnane derivatives of the general formula (I) which comprises cultivating, in a medium containing deoxycholic acid and/or a salt thereof, a microbe belonging to the genus Alcaligenes or Pseudomonas and being capable of producing the pregnane derivatives of the general formula (I) by utilizing deoxycholic acid and/or a salt thereof as the substrate.

DETAILED DESCRIPTION OF THE INVENTION

The microbes to be used in the present invention may be wild-type strains of the genus Alcaligenes or Pseudomonas or mutants thereof obtained by natural mutation or a conventional mutagenic treatment such as x-ray irradiation, ultraviolet irradiation, treatment with a chemical mutagen such as N-methyl-N'-nitro-N-nitrosoguanidine, 4-nitroquinoline-N-oxide, acriflavine or ethyl methanesulfonate, or combination thereof and the like.

Among the microbes obtained by the present inventors and being capable of producing the pregnane derivatives of the general formula (I) by utilizing deoxycholic acid or a salt thereof as the substrate, the representatives have been deposited with the Fermentation Research Institute, Agency of Industrial Science and Technology, Japan (hereinafter, referred to as FERM). They are the strains *Alcaligenes faecalis* D4020-K15 (FERM BP-204) and *Pseudomonas putida* D4014-A357 (FERM BP-206). *Alcaligenes faecalis* D4020-K15 is a mutant of *Alcaligenes faecalis* D4020 (FERM BP-182) which is a wild-type strain isolated from soil, and *Pseudomonas putida* D4014-A357 is a mutant of *Pseudomonas putida* D4014 (FERM BP-205) which is a wild-type strain isolated from soil.

The morphological, cultural and physiological characteristics of these strains are shown in Table 1 and Table 2.

TABLE 1

| Taxonomical character | Alcaligenes faecalis D4020 | Alcaligenes faecalis D4020-K15 |
|---|---|---|
| Morphological characteristics | | |
| Form | Rods | Rods |
| Size | 0.5 × 1.2~1.7μ | 0.5 × 1.0~1.7μ |
| Flagellum | Peritrichous flagella | Peritrichous flagella |
| Spore | Nil | Nil |
| Gram stain | Negative | Negative |
| Acid fast stain | Nil | Nil |
| Cultural characteristics | | |
| Bouillon agar plate culture | Circular, opaque, convex | Circular, opaque, convex |
| Bouillon agar slant culture | Moderate growth, filiform, pigment not produced | Moderate growth, filiform, pigment not produced |
| Bouillon broth | Moderate turbidity, pellicle | Moderate turbidity |
| Temperature for growth | Growth at 37° C., poor growth at 41° C. | Growth at 37° C., poor growth at 41° C. |
| Gelatin stab | No liquefaction | No liquefaction |

TABLE 1-continued

| Taxonomical character | *Alcaligenes faecalis* D4020 | | *Alcaligenes faecalis* D4020-K15 | |
|---|---|---|---|---|
| Litmus milk | Alkaline, milk unchanged | | Alkaline, milk unchanged | |
| BCP milk | Alkaline, milk unchanged | | Alkaline, milk unchanged | |
| Physiological characteristics (Note 1) | | | | |
| Nitrate reduction | + | | + | |
| Denitrification | − | | − | |
| Methyl red test | − | | − | |
| Voges-Proskauer test | − | | − | |
| Indole production | − | | − | |
| Hydrogen sulfide production | − | | − | |
| Starch hydrolysis | − | | − | |
| Citrate utilization | + | | + | |
| Assimilation of inorganic nitrogen sources | + | | + | |
| Urease | ± | | ± | |
| Oxidase | + | | + | |
| Catalase | + | | + | |
| Require of oxygen | Aerobic | | Aerobic | |
| Oxidation/Fermentation test | Oxidative | | Oxidative | |
| Production of acids and gases from carbohydrates (Note 2) | Production of acids | Evolution of gases | Production of acids | Evolution of gases |
| (1) L-Arabinose | + | − | + | − |
| (2) D-Xylose | + | − | + | − |
| (3) D-Glucose | + | − | + | − |
| (4) D-Mannose | + | − | + | − |
| (5) D-Fructose | − | − | − | − |
| (6) D-Galactose | + | − | + | − |
| (7) Maltose | − | − | − | − |
| (8) Sucrose | − | − | − | − |
| (9) Lactose | − | − | − | − |
| (10) Trehalose | − | − | − | − |
| (11) D-Sorbitol | − | − | − | − |
| (12) D-Mannitol | − | − | − | − |
| (13) Inositol | − | − | − | − |
| (14) Glycerol | − | − | − | − |
| (15) Starch | − | − | − | − |

TABLE 2

| Taxonomical character | *Pseudomonas putida* D4014 | | *Pseudomonas putida* D4014-A357 | |
|---|---|---|---|---|
| Morphological characteristics | | | | |
| Form | Rods | | Rods | |
| Size | 0.5~0.6 × 1.5~2.9μ | | 0.5 1.5~2.5μ | |
| Flagellum | Polar flagella | | Polar flagella | |
| Spore | Nil | | Nil | |
| Gram stain | Negative | | Negative | |
| Acid fast stain | Nil | | Nil | |
| Cultural characteristics | | | | |
| Bouillon agar plate culture | Circular, raised, convex, smooth, entire | | Circular, raised, convex, smooth, entire | |
| Bouillon agar slant culture | Moderate growth, filiform, translucent, fluorescent | | Moderate growth, filiform, translucent, fluorescent | |
| Bouillon broth | Turbid, pellicle | | Turbid | |
| Temperature for growth | Growth at 37° C. | | Growth at 37° C. | |
| Gelatin stab | No liquefaction | | No liquefaction | |
| Litmus milk | Alkaline, milk unchanged | | Alkaline, milk unchanged | |
| BCP milk | Alkaline, milk unchanged | | Alkaline, milk unchanged | |
| Physiological characteristics (Note 1) | | | | |
| Nitrate reduction | − | | − | |
| Denitrification | − | | − | |
| Methyl red test | + | | + | |
| Voges-Proskauer test | − | | − | |
| Indole production | − | | − | |
| Hydrogen sulfide production | − | | − | |
| Starch hydrolysis | − | | − | |
| Citrate utilization | + | | + | |
| Assimilation of inorganic nitrogen sources | + | | + | |
| Urease | ± | | ± | |
| Oxidase | + | | + | |
| Catalase | + | | + | |
| Arginine dihydrolase | + | | + | |
| Require of oxygen | Aerobic | | Aerobic | |
| Oxidation/Fermentation test | Oxidative | | Oxidative | |
| Production of acids and gases from carbohydrates (Note 2) | Production of acids | Evolution of gases | Production of acids | Evolution of gases |
| (1) L-Arabinose | + | − | + | − |
| (2) D-Xylose | + | − | + | − |

TABLE 2-continued

| Taxonomical character | Pseudomonas putida D4014 | | Pseudomonas putida D4014-A357 | |
|---|---|---|---|---|
| (3) D-Glucose | + | − | + | − |
| (4) D-Mannose | + | − | + | − |
| (5) D-Fructose | − | − | − | − |
| (6) D-Galactose | + | − | + | − |
| (7) Maltose | − | − | − | − |
| (8) Sucrose | − | − | − | − |
| (9) Lactose | − | − | − | − |
| (10) Trehalose | − | − | − | − |
| (11) D-Sorbitol | − | − | − | − |
| (12) D-Mannitol | − | − | − | − |
| (13) Inositol | − | − | − | − |
| (14) Glycerol | − | − | − | − |
| (15) Starch | − | − | − | − |

Remarks:
(Note 1) The symbols used under Physiological characteristics indicate the following:
+: The strain has the corresponding characteristics or produces the correspondng product.
±: It is difficult to determine whether the strain has the corresponding characterstics or produces the corresponding product or not.
−: The strain neither has the corresponding characteristics nor produces the correspondingproduct.
(Note 2) By using Hugh and Leifson medium in which each of the carbohydrates shown in Table I and Table 2 was used in lieu of the carbon source thereof, production of acids and gases by the strain was observed.
+: An acid or a gas is produced.
±: It is difficult to determine whether an acid or a gas is produced or not.
−: Neither an acid nor a gas is produced.

On the basis of these morphological, cultural and physiological characteristics, the strains have been classified according to Bergey's Manual of Determinative Bacteriology, 7th and 8th Editions.

The strain *Alcaligenes faecalis* D4020 has been identified as a strain of the genus Alcaligenes based on its morphological characteristics, among others, that it is a rod having peritrichous flagella and that it reacts negative in Gram staining as well as on the physiological characteristics, among others, that it reacts positive in the oxidase and catalase reactions, that it is aerobic and that the oxidation/fermentation test gives oxidative results, and further identified as a strain of the species *Alcaligenes faecalis* based on the facts that it does not liquefy gelatin, that milk becomes alkaline but otherwise remains unchanged and that it does not cause denitrification. Generally, a mutant is considered to belong to the same species as its parent strain belongs to. Accordingly, the strain *Alcaligenes faecalis* D4020-K15 has been judged as belonging to the species *Alcaligenes faecalis*.

The strain *Pseudomonas putida* D4014 has been identified as a strain of the genus Pseudomonas based on its morphological characteristics, among others, that it is a rod having polar flagella and that Gram staining gives negative results as well as on the physiological characteristics, among others, that the oxidase and catalase reactions each gives positive results, that it is aerobic and that the oxidation/fermentation test results are oxidative. Furthermore, the strain *Pseudomonas putida* D4014 has been identified as a strain of the species *Pseudomonas putida* in view of the facts, among others, that the slant culture exhibits fluorescence, that it does not liquefy gelatin, that it grows at 37° C. and that it produces arginin dihydrolase. Since a mutant is generally considered to belong to the same strain as the parent strain belongs to, the strain *Pseudomonas putida* D4014-A357 has been judged to belong to the species *Pseudomonas putida*.

The process of the present invention is carried out by cultivating a microbe of the genus Alcaligenes or Pseudomonas, which is capable of producing the pregnane derivative of the general formula (I) by utilizing deoxycholic acid or a salt thereof as the substrate, in a culture medium containing said substrate.

In accordance with the present invention, deoxycholic acid per se can be used as the substrate. There can also be used an alkali metal salt of deoxycholic acid such as sodium deoxycholate, potassium deoxycholate or the like or an alkaline earth metal salt of deoxycholic acid such as calcium deoxycholate, magnesium deoxycholate or the like; preferred in a alkali metal salt. When a deoxycholate is used, it is dissolved in water to prepare an aqueous solution containing the deoxycholate in a predetermined concentration. Alternatively, a certain amount of an alkali metal compound or an alkaline earth metal compound which forms a salt with deoxycholic acid may previously be dissolved in water and thereto is added deoxycholic acid to give an aqueous solution containing a deoxycholate is a predetermined concentration.

In general, the concentration of the substrate in a culture medium may be varied widely in the range of from about 1 to 200 g/l as deoxycholic acid. However, from the viewpoints of the yield of the desired product, cultivation conditions and economic efficiency such as operability or workability, it is preferable to use the substrate in a concentration of about 2 to 50 g/l as deoxycholic acid.

The cultivation can be carried out according to a known method under aerobic conditions and shake or submerged culture using a liquid medium is generally employed.

As the medium, there can be used one containing nutrients which can be assimilated by the microbe to be used. The medium may contain deoxycholic acid or a salt thereof as the sole carbon source. Optionally, it may contain an additional carbon source such as glucose, glycerol, peptone, meat extract, yeast extract, etc. or a mixture thereof. Generally, the additional carbon source can be added to the medium in a concentration of about 0.1 to 20 g/l. As a nitrogen source, there can be used an inorganic nitrogen source such as ammonium sulfate, ammonium chloride, ammonium phosphate, ammonium nitrate, sodium nitrate, potassium nitrate, etc.; an organic nitrogen source such as polypeptone, peptone, meat extract, etc.; or a mixture thereof. Generally, the nitrogen source can be added to the medium in a concentration of about 0.5 to 5 g/l. In addition, an inorganic salt such a dipotassium hydrogen phosphate, potassium dihydrogen phosphate, magnesium sulfate, manganese sulfate, zinc sulfate, cobalt chloride, sodium molybdate, cuprice sulfate, calcium chloride, sodium chloride, etc. or a mixture thereof can be added to the medium.

The cultivation conditions are not very critical. Generally, the cultivation can be carried out in the manner of shake or submerged culture at a pH of about 7 to 9 at about 25° to 35° C. for about 10 hours to 7 days to cause production and accumulation of the pregnane derivative of the general formula (I) in the medium.

When a strain of the genus Alcaligenes is cultivated in accordance with the method of the present invention, deoxycholic acid and/or a salt thereof used as the substrate is converted to a pregnane derivative of the general formula (I) in which the dotted line-marked site involves a double bond, namely 12-hydroxypregna-1,4-dien-3-one-20-carbaldehyde. In that case, the production of 12α-hydroxypregna-1,4-dien-3-one-20-carbaldehyde generally predominates, whereas 12β-hydroxypregna-1,4-dien-3-one-20-carbaldehyde is produced rather as a byproduct. However, when the cultivation is conducted under conditions such that the conversion of deoxycholic acid and/or a slat thereof is relatively slow and/or when the cultivation is carried out in a short period of time, the yield of 12β-hydroxypregna-1,4-dien-3-one-20-carbaldehyde increases. When a strain of the genus Pseudomonas is used, deoxycholic acid and/or a salt thereof is converted to a pregnane derivative of the general formula (I) in which no double bond is present at the dotted-line-marked site, namely 12-hydroxypregna-4-en-3-one-20-carbaldehyde. In this case, 12α-hydroxypregna-4-en-3-one-20-carbaldehyde is obtained selectively.

The pregnane derivative of the general formula (I) as accumulated in the culture broth generally precipitates out in the broth, since the solubility thereof in water is by far smaller as compared with the substrate, namely deoxycholic acid or a salt thereof. To harvest this pregnane derivative, the precipitate is separated from the broth containing suspended cells either by decanting or by the steps of centrifuging the broth at the speed that will not cause sedimentation of the suspended cells to additionally obtain a sediment of the pregnane derivative and then decanting. From the remaining broth, the cells and other insoluble matters are removed by filtration or centrifugation and the resulting filtrate or supernatant is made alkaline with an alkali such as sodium hydroxide, potassium hydroxide or calcium hydroxide, for instance, followed by extraction with a water-immiscible organic solvent capable of dissolving said pregnane derivative, e.g. ethyl acetate, chloroform or a mixture of chloroform and methanol. The extracts are pooled and the solvent is distilled off, whereby the pregnane derivative still remaining dissolved in the broth can be recovered. The above extraction with an organic solvent can be applied not only to the filtrate or supernatant but also to the broth as such. The sediment or extract obtained in the above manner is substantially free from residues of the substrate deoxycholic acid and/or salt thereof or any byproducts, so that a high purity grade of the pregnane derivative of the general formula (I) can be easily obtained therefrom, for example by recrystallization from aqueous methanol. The separation of a mixture of 12α-hydroxypregna-1,4-dien-3-one-20-carbaldehyde and 12β-hydroxypregna-1,4-dien-3-one-20-carbaldehyde into 12α-hydroxypregna-1,4-dien-3-one-20-carbaldehyde and 12β-hydroxypregna-1,4-dien-3-one-20-carbaldehyde is carried out by allowing the above mixture to be adsorbed on a silica gel column followed by elution with a mixed solvent composed of chloroform and ethanol. 12β-Hydroxypregna-1,4-dien-3-one-20-carbaldehyde is first eluted and then 12α-hydroxypregna-1,4-dien-3-one-20-carbaldehyde is eluted. Each aldehyde can be recovered by distilling off the solvent from the eluate under reduced pressure.

The pregnane derivative of the general formula (I) thus obtainable according to the method of the present invention, if necessary after acylation of the hydroxyl group at position 12, can be derived to a 12-substituted-$\Delta^4$ or $\Delta^{1,4}$-pregnane-3,20-dione of the general formula

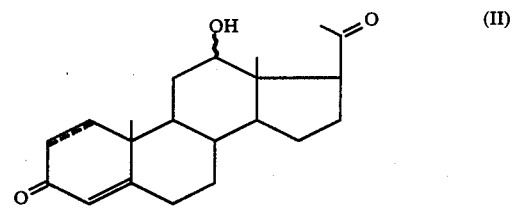

wherein R is a hydrogen atom or an acyl group, and the dotted line and wavy line are as defined above, in a per se conventional manner by reacting with a secondary amine such as piperidine or pyrrolidine and oxidizing the resulting enamine with ozone or chromium trioxide, for instance. The 12-substituted-$\Delta^4$ or $\Delta^{1,4}$-pregnane-3,20-dione can be converted to a $\Delta^{4,11(12)}$ or $\Delta^{1,4,11(12)}$-pregnane-3,20-dione of the general formula

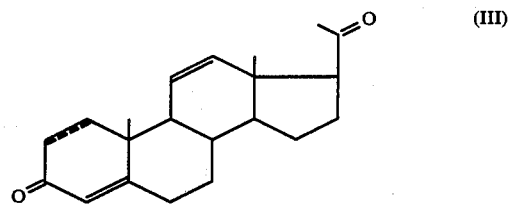

wherein the dotted line has the same meaning as above, by directed elimination of carboxylic acid or by conventional sulfonation, if necessary following hydrolysis, and elimination of sulfonic acid. The $\Delta^{1,4,11(12)}$-pregnane-3,20-dione is a known compound, whereas the $\Delta^{4,11(12)}$-pregnane-3,20-dione can be derived to said $\Delta^{1,4,11(12)}$-pregnane-3,20-dione by conventional dehydrogenation. The $\Delta^{4,11(12)}$ or $\Delta^{1,4,11(12)}$-pregnane-3,20-dione represented by the general formula (III) can further be derived to prednisone and further to prednisolone or hydrocortisone in a conventional manner as shown, for instance, by the following reaction scheme:

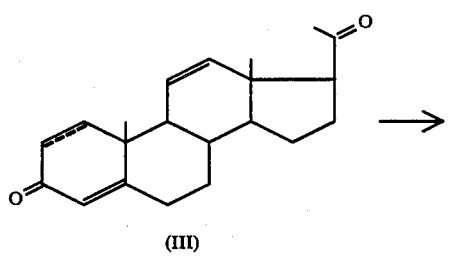

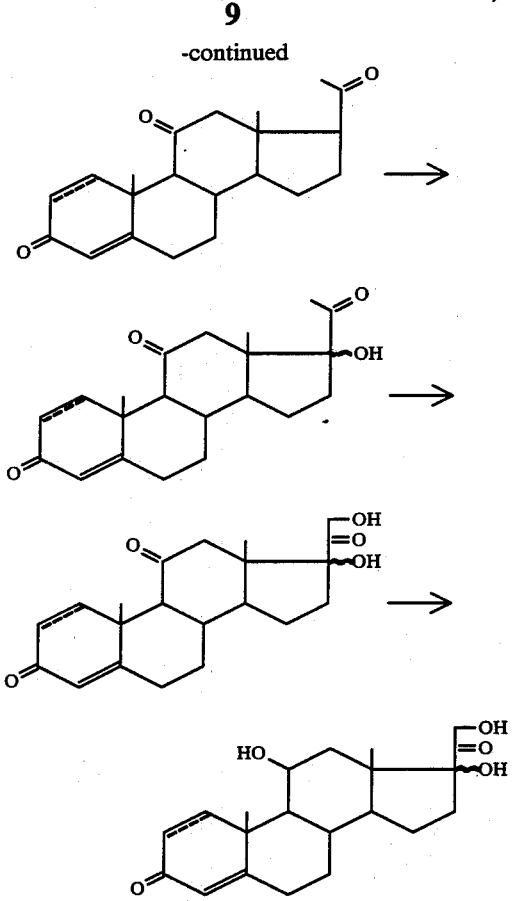

wherein the dotted line has the same meaning as above.

The following examples and reference examples further illustrate the present invention in detail but are not to be construed to limit the scope thereof.

Preparation of mutants

Preparation of the strain *Alcaligenes faecalis* D4020-K15

*Alcaligenes faecalis* D4020 was grown on a slant of medium 1 (composition: 0.5% deoxycholic acid, 0.05% sodium hydroxide, 0.5% peptone, 0.5% yeast extract, 0.5% sodium chloride and 1.5% agar). A loopful of the microbe so grown was used for inoculating 10 ml of medium 2 (composition: 2% deoxycholic acid, 0.2% sodium hydroxide, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), and shake-cultured at 30° C. for 8-10 hours. A 0.3-ml-portion o the culture was added to 10 ml of medium 3 (composition: 0.5% deoxycholic acid, 0.5% sodium hydroxide, 0.1% glucose, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), followed by incubation at 30° C. for 10-15 hours. The cells, which were in the logarithmic growth phase, were collected aseptically by filtration using a membrane filter (pore size: 0.45μ), washed with 20 ml of 0.1M phosphate buffer (pH 7.0) and suspended in 25 ml of the same buffer. To the suspension was added N-methyl-N'-nitro-N-nitrosoguanidine to a final concentration of 20 μg/ml. The mixture was shaken at 30° C. for 10-15 minutes. The cells so subjected to mutagenic treatment were collected by filtration using a membrane filter (pore size: 0.45μ), washed with 20 ml of 0.1M phosphate buffer (pH 7.0) and suspended in 20 ml of the same buffer. The resulting suspension was diluted with sterilized physiological saline solution and the dilution was applied to an agar plate made of medium 4 (composition: 0.5% deoxycholic acid, 0.05% sodium hydroxide, 0.2% ammonium nitrate, 0.1% potassium dihydrogen phosphate, 0.6% dipotassium hydrogen phosphate, 0.02% magnesium sulfate heptahydrate, 0.02% yeast extract and 1.5% agar) so that 500 to 1,000 colonies could appear on the plate. The incubation was then performed at 30° C. for 3-4 days. Among the colonies that had appeared, pin point colonies were transferred to a slant made of medium 1, and one loopful thereof was used to inoculate 10 ml of medium 5 (composition: 0.2% deoxycholic acid, 0.02% sodium hydroxide, 0.1% glucose, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), followed by shake culture at 30° C. for 24 hours. The products in each culture obtained in this manner were examined by thin layer chromatography. A strain capable of selectively accumulating 12α-hydroxypregna-1,4-dien-3-one-20-carbaldehyde under the above cultural conditions was found and named *Alcaligenes faecalis* D4020-K15.

Preparation of the strain *Pseudomonas putida* D4014-A357

A loopful of *Pseudomonas putida* D4014 grown on a slant of the above-mentioned medium 1 was used for inoculating 10 ml of the above-mentioned medium 2 preliminarily prepared in a test tube (200 mm×21 mm in diameter), and shake-cultured at 30° C. for 14-15 hours. A 0.3 ml portion of the culture was added to 10 ml of the above-mentioned medium 3 preliminarily prepared in a test tube (200 mm×21 mm in diameter), followed by incubation at 30° C. for 8-9 hours. The cells, which were in the logarithmic growth phase, were aseptically collected with a membrane filter (pore size: 0.45μ), washed with 20 ml of 0.1M phosphate buffer (pH 7.0) and suspended in 25 ml of the same buffer. To the suspension was added N-methyl-N'-nitro-N-nitrosoguanidine to a final concentration of 50 μg/ml, and the mixture was allowed to stand for 3-4 minutes. The cells, which had been subjected to the above mutagenic treatment, were collected with a membrane filter (pore size: 0.45μ), washed with 20 ml of 0.1M phosphate buffer (pH 7.0) and suspended in 20 ml of the same buffer. The resulting suspension was diluted with sterilized physiological saline solution and the dilution was applied to an agar plate of the above-mentioned medium 4 to the extent such that 500-1,000 colonies could appear thereon. After incubation at 30° C. for 3-4 days, pin point colonies among those that had appeared were isolated and transferred to a slant of medium 1 and a loopful thereof was used to inoculate 10 ml of the above-mentioned medium 5 preliminarily prepared in a test tube (200 mm×21 mm in diameter). The inoculated medium was shaken at 30° C. for 24 hours. The products in each culture thus obtained were examined by thin layer chromatography. In this manner, a strain capable of selectively accumulating 12α-hydroxypregna-4-en-3-one-20-carbaldehyde under the above cultural conditions was obtained and named *Pseudomonas putida* D4014-A357.

EXAMPLE 1

*Alcaligenes faecalis* D4020-K15 (FERM BP-204) was cultivated in the following manner. A medium (pH 8.4) was prepared by adding tap water to 1.0 g of deoxycholic acid, 0.1 g of glucose, 0.2 g of ammonium nitrate, 0.12 g of potassium dihydrogen phosphate, 0.61 g of dipotassium hydrogen phosphate, 0.02 g of magnesium sulfate heptahydrate, 0.02 g of yeast extract and 0.1 g of sodium hydroxide, to a volume of 100 ml. A 10 ml portion of this medium was placed in each of 10 test tubes (200 mm×21 mm in diameter) and steam-sterilized at 120° C. for 15 minutes. Separately and in advance, the above strain was grown in the same medium as above on a test tubeshaker for one day, and a 0.5 ml portion of the thus obtained seed culture was added to each of the above-mentioned test tubes (200 mm×21 mm in diameter) and shake-cultured at 30° C. for 2 days. The pooled culture broth was centrifuged, whereby a mixture of the cells and a precipitate which had formed in the course of cultivation was separated from a culture supernatant. To said mixture was added a 1N aqueous solution of sodium hydroxide to adjust the resulting mixture to pH 9, and the mixture was extracted with 200 ml of ethyl acetate Separately, the culture supernatant was adjusted to pH 9 by adding a 1N aqueous solution of sodium hydroxide, and extracted with 200 ml of ethyl acetate. This extract and the extract obtained in the above extraction were combined and dried over anhydrous sodium sulfate, and the ethyl acetate was distilled off using a rotary evaporator to give 750 mg of a mixture of 12$\beta$-hydroxypregna-1,4-dien-3-one-20-carbaldehyde and 12$\alpha$-hydroxypregna-1,4-dien-3-one-20-carbaldehyde.

A portion of the thus-obtained mixture was taken, and methanol was added thereto to prepare a 1% solution. A 25-$\mu$l portion of this solution was injected into a high performance liquid chromatograph equipped with a $\mu$Bondapak C-18 column (HLC-GPC-244 type manufactured by Waters Associates in U.S.A.). A 25:75 (by volume) water-methanol mixture adjusted to pH 4.0 was used as the mobile phrase at a flow rate of 1 ml/minute. The detection was made by the refractive index method. The areas of the chromatographic peaks obtained were measured with an integrator (Shimadzu Chromato-Pack C-RIA manufactured by Shimadzu Corporation in Japan) and it was indicated that the peak areas for 12$\beta$-hydroxypregna-1,4-dien-3-one-20-carbaldehyde and 12$\alpha$-hydroxypregna-1,4-dien-3-one-20-carbaldehyde accounted for 95% of the total peak area. In the above mixture, the ratio between 12$\beta$-hydroxypregna-1,4-dien-3-one-20-carbaldehyde and 12$\alpha$-hydroxypregna-1,4-dien-3-one-20-carbaldehyde was $\frac{1}{4}$.

From the product mixture obtained according to the same procedure as mentioned above 12$\beta$-hydroxypregna-1,4-dien-3-one-20-carbaldehyde and 12$\alpha$-hydroxypregna-1,4-dien-3-one-20-carbaldehyde were respectively isolated in the following manner. First, a tubular column, 2.6 cm in inside diameter and 70 cm in length, was packed with a suspension of about 100 g of silica gel in about 200 ml of chloroform. Separately, 1.2 g of the above product mixture was dissolved in about 20 ml of chloroform and insolubles were removed. The chloroform solution was concentrated to about 5 ml and then allowed to be adsorbed on the above silica gel column and eluted in sequence with chloroform, a 99:1 (by volume) chloroform-ethanol mixture and a 97:3 (by volume) chloroform-ethanol mixture. 12$\beta$-Hydroxypregna-1,4-dien-3-one-20-carbaldehyde was eluted in a fraction covering about the 250 ml to 280 ml portions of the second eluate, i.e. the 99:1 chloroformethanol mixture, and thereafter 12$\alpha$-hydroxypregna-1,4-dien-3-one-20-carbaldehyde was eluted with the same eluate in a fraction of about 450 ml to 510 ml. These two aldehydes were discriminated from each other based on the facts that, in thin layer chromatography using a thin layer plate (silica gel 60, F-254 manufactured by Merck in U.S.A.) and an isooctaneethyl acetate-acetic acid mixture (10:10:2 by volume) as the developing solvent, 12$\beta$-hydroxypregna-1,4-dien-3-one-20-carbaldehyde gives a spot corresponding to $R_f$=about 0.4 and 12$\alpha$-hydroxypregna-1,4-dien-3-one-20-carbaldehyde gives a spot corresponding to $R_f$=about 0.34. The chloroform and ethanol were distilled off from each eluate fraction with a rotary evaporator, and the residue was washed with diethyl ether and dried. There were thus obtained about 80 mg of 12$\beta$-hydroxypregna-1,4-dien-3-one-20-carbaldehyde and about 360 mg of 12$\alpha$-hydroxypregna-1,4-dien-3-one-20-carbaldehyde.

The 12$\beta$-hydroxypregna-1,4-dien-3-one-20-carbaldehyde and 12$\alpha$-hydroxypregna-1,4-dien-3-one-20-carbaldehyde were identified based on the following data:

12$\beta$-Hydroxypregna-1,4-dien-3-one-20-carbaldehyde

Melting point: 157°–161° C.

Mass spectrum (m/Z): 342 [M]$\dagger$, 324 [M—H$_2$O]$\dagger$, 309 [M—H$_2$O—CH$_3$]$\dagger$ The presence of 3-keto-1,4-dien was confirmed by m/Z=121 and 122.

NMR spectrum (90 MHz) $\delta_{HMS}^{DMSO-d6}$ 0.68 (3H, s) 18-CH$_3$ 0.90 (3H, d, J=6.3 Hz) 21-CH$_3$ 1.16 (3H, s) 19-CH$_3$ 3.25 (1H, s) 12$\beta$-OH 3.40 (1H, m) 12$\alpha$-H 5.95 (1H, s) 4-H 6.15 (1H, dd, J=18 Hz, J=3 Hz) 2-H 7.13 (1H, d, J=12 Hz) 1-H 9.50 (1H, d, J=9 Hz) 22-CHO 12$\alpha$-Hydroxypregna-1,4-dien-3-one-20-carbaldehyde Melting point: 194°–201° C.

Mass spectrum (m/Z): 342 [M]$\dagger$, 324 [M-H$_2$O]$\dagger$, 309 [M-H$_2$O-CH$_3$]$\dagger$ The presence of 3-keto-1,4-dien was confirmed by m/Z=121 and 122.

NMR spectrum (90 MHz) $\delta_{HMS}^{DMSO-d6}$: 0.71 (3H, s) 18-CH$_3$ 1.09 (3H, d) 21-CH$_3$ 1.17 (3H, s) 19-CH$_3$ 3.83 (1H, t, J=3 Hz) 12$\beta$-H 4.33 (1H, d) 12$\alpha$-OH 5.95 (1H, s) 4-H 6.08 (1H, d, J=10 Hz)2-H 7.08 (1H, d, J=10 Hz)1-H 9.56 (1H, s)22-CHO

EXAMPLE 2

*Alcaligenes faecalis* D4020-K15 (FERM BP-204) was cultivated in the following manner. A medium (pH 8.4) was prepared by adding tap water to 1.0 g of deoxycholic acid, 0.1 g of glucose, 0.2 g of ammonium nitrate, 0.12 g of potassium dihydrogen phosphate, 0.61 g of dipotassium hydrogen phosphate, 0.02 g of magnesium sulfate heptahydrate, 0.02 g of yeast extract and 0.1 g of sodium hydroxide to a volume of 100 ml. This medium was placed in a 500 ml Sakaguchi flask and steam-sterilized at 120° C. for 15 minutes. Separately and in advance, the above microbe was grown in the same medium as above on a test tube shaker for one day and a 10 ml portion of the seed culture was added to the above-mentioned 500-ml Sakaguchi flask. The flask was shaken at 30° C. for 2 days. The thus-obtained culture broth was centrifuged to separate a mixture of the cells and the precipitate which had formed during the incubation from the culture supernatant. An aqueous 1 N sodium hydroxide solution was added to said mixture in an amount sufficient to adjust the pH to 9, and the resultant mixture was extracted with 200 ml of ethyl acetate. On the other hand, the culture supernatant was adjusted to pH 9 by adding an aqueous 1N sodium hydroxide solution and then extracted with 200 ml of ethyl acetate. Both the extracts were combined and dried over anhydrous sodium sulfate, and the ethyl acetate was distilled off in a rotary evaporator to give 700 mg of 12α-hydroxypregna-1,4-dien-3-one-20-carbaldehyde.

A portion of the thus-obtained 12α-hydroxypregna-1,4-dien-3-one-20-carbaldehyde was dissolved in methanol to prepare a 1% solution, and a 25-μl portion of the solution was injected into a high performance liquid chromatograph equipped with a μBondapak C-18 column (as mentioned hereinbefore). A 25:75 (by volume) water-methanol mixture adjusted to pH 4.0 was used as the mobile phase at a flow rate of 1 ml/min. The detection was made by the refractive index method. The areas of the chromatographic peaks obtained were measured with an integrator (as mentioned hereinbefore). Area ratio indicated that the above 12α-hydroxypregna-1,4-dien-3-one-20-carbaldehyde was 96% pure.

The identification of the above product as 12α-hydroxypregna-1,4-dien-3-one-20-carbaldehyde was carried out in the same manner as in Example 1.

EXAMPLE 3

*Pseudomonas putida* D4014-A357 (FERM BP-206) was cultivated in the following manner. A medium was prepared by adding 50 ml of tap water to 0.2 g of deoxycholic acid, 0.1 g of glucose, 0.2 g of ammonium nitrate, 0.1 g of potassium dihydrogen phosphate, 0.6 g of dipotassium hydrogen phosphate, 0.02 g of magnesium sulfate heptahydrate and 0.02 g of yeast extract, adjusting the solution to pH 8.4 with 1N sodium hydroxide and further adding water to make the volume 100 ml. This medium was placed in a 500 ml Sakaguchi flask and steam-sterilized at 120° C. for 15 minutes. Separately and in advance, the above microbe was grown in the same medium as above on a test tube shaker for one day and a 10 ml portion of the seed culture was added to the above 500 ml Sakaguchi flask, followed by shake culture at 30° C. for 2 days. The precipitate which had formed during the cultivation and the cells were collected by centrifugation and washed with water, and 50 ml of methanol was added thereto to dissolve the precipitate to a satisfactory extent. Recentrifugation gave a supernatant methanol solution. The methanol was distilled off with a rotary evaporator to give 65 mg of 12α-hydroxypregna-4-en-3-one-20-carbaldehyde.

A portion of the thus-obtained 12α-hydroxypregna-4-en-3-one-20-carbaldehyde. was dissolved in methanol in a concentration of 4%, and a 25 μl portion of the solution was injected into a high performance liquid chromatograph equipped with a μBondapak C-18 column (as mentioned hereinbefore). A 30:70 (by volume) water-methanol mixture adjusted to pH 4.0 was used as the mobile phase at a flow rate of 1 ml/min. The refractive index-based detection method was employed. The areas of the chromatographic peaks obtained were measured with an integrator (as mentioned hereinbefore). The purity of the above 12α-hydroxypregna-4-en-3-one-20-carbaldehyde as determined by area ratio calculation was 98%.

The identification of the above product as 12α-hydroxypregna-4-en-3-one-20-carbaldehyde was based on the following data:
Melting point: 179°–181° C.
Mass spectrum (m/Z): 344 [M]$\dot{+}$ 326 [M-H$_2$O]$\dot{+}$ 316 [M-CO]$\dot{+}$.
The presence of 3-keto-4-ene was confirmed by m/Z=124.
NMR spectrum (90 MHz) $\delta_{HMS}^{CDCl_3}$: 0.72 (3H, s) 18-CH$_3$ 1.10 (3H, d) 21-CH$_3$ 1.15 (3H, s) 19-CH$_3$ 3.95 (1H, s) 12β-H 5.70 (1H, s) 4-H 9.40 (1H, d) 22-CHO.

Reference Example

Synthesis of 12α-hydroxypregna-1,4-diene-3,20-dione

12α-Hydroxypregna-1,4-dien-3-one-20-carbaldehyde (34.2 g) was dissolved in 300 ml of methylene chloride. To the solution were added 23.6 g of acetyl chloride and 27.7 g of pyridine, and the mixture was stirred at room temperature for 5 hours. To the reaction mixture was added 300 ml of methylene chloride, the resulting solution was washed in sequence with diluted hydrochloric acid and water, and dried over anhydrous magnesium sulfate. Low-boiling fractions were distilled off from the solution under reduced pressure. There was thus obtained crude 12α-acetoxypregna-1,4-dien-3-one-20-carbaldehyde as a viscous substance. This crude product was dissolved in 300 ml of benzene, 21.3 g of piperidine was added to the solution, and the resulting mixture was refluxed for 3 hours while removing the byproduct water azeotropically with benzene. Low-boiling fractions were distilled off from the thus-obtained reaction mixture. There remained crude 12α-acetoxy-22-(N-peridyl)bisnor-1,4,20(22)-cholatrien-3-one as a viscous substance, which was dissolved in 180 ml of pyridine. To the solution was added gradually at room temperature a mixture of 20.0 g of chromium trioxide and 250 ml of pyridine. After stirring the resulting mixture for one hour, 1 liter of benzene was added to the reaction mixture. The solid matter was filtered off, and diluted hydrochloric acid was added to the filtrate. After effecting benzene extraction to a sufficient extent, the benzene layer was washed in sequence with diluted hydrochloric acid and water. Low-boiling fractions were distilled off under reduced pressure, and the residue was purified by preparative liquid chromatography [column: Waters Associates' Prep LC/System 500, Prep PAK TM 500/SILICA; solvent system: isopropyl alcohol:n-hexan=20:80, v/v] to give 9.1 g of 12α-acetoxypregna-1,4-diene-3,20-dione as crystals. It has the following physical properties.
Melting point: 175°–176° C.
NMR spectrum (90 MHz) $\delta_{HMS}^{CDCl_3}$: 0.76, 1.20, 2.0, 2.06 (each s, each 3H); 5.10–5.22 (m, 1H); 6.07 (bs, 1H); 6.18, 6.20 (each d, 1H); 6.93 (d, 1H).

To a solution of 2.2 g of potassium hydroxide in 80 ml of methanol was added 7.4 g of 12α-acetoxypregna-1,4-diene-3,20-dione, and the mixture was stirred at room temperature for 10 hours. The reaction mixture was concentrated to about one tenth the original volume by distilling off the methanol under reduced pressure. To the concentrated reaction mixture was added 150 ml of benzene, and the solution was washed in sequence with water, diluted hydrochloric acid and water and then dried over anhydrous magnesium sulfate. Low-boiling fractions were distilled off under reduced pressure and the residue was recrystallized from ethyl acetate to give 5.4 g of 12α-hydroxypregna-1,4-diene-3,20-dione (Gas chromatographic analysis revealed that purity thereof was 90%). It has the following physical properties.
Melting point: 185°–186° C.
NMR spectrum (90 MHz) $\delta_{HMS}^{CDCl_3}$: 0.69, 1.17, 2.14 (each s, each 3H); 4.04–4.16 (m, 1H); 6.06 (bs, 1H); 6.16, 6.18 (each d, 1H); 7.03 (d, 1H).

Synthesis of pregna-1,4,11(12)-triene-3,20-dione

12α-Hydroxypregna-1,4-diene-3,20-dione (3.3 g) was dissolved in 17 ml of pyridine. To the solution was added 3.4 g of methanesulfonyl chloride, and the mixture was stirred at room temperature for 8 hours. The reaction mixture was then poured into 300 ml of diluted hydrochloric acid, and the resulting mixture was extracted with three 300 ml portions of benzene. The extracts were combined and washed in sequence with diluted hydrochloric acid, aqueous sodium bicarbonate solution and water, and dried over anhydrous magnesium sulfate. Low-boiling fractions were distilled off under reduced pressure from the extract to give 3.8 g of crude 12α-mesyloxypregna-1,4-diene-3,20-dione, which was recrystallized from ethyl acetate. The physical properties for the thus-purified product were as follows:
Melting point: 185°–186° C.
NMR spectrum (90 MHz) $\delta_{HMS}^{CDCl_3}$: 0.82, 1.18, 2.10, 2.96 (each s, each 3H); 5.04–5.16 (m, 1H); 6.05 (bs, 1H); 6.19, 6.21 (each d, 1H); 6.95 (d, 1H).

12α-Mesyloxypregna-1,4-diene-3,20-dione (3.0 g) was dissolved in 60 ml of hexamethylphosphoramide. To the solution was added 7.2 g of potassium acetate, and the mixture was stirred at 120° C. for 5 hours. To the reaction mixture was added 300 ml of diluted hydrochloric acid, and the whole mixture was extracted with three 200 ml portions of benzene. The extracts were combinedly washed in sequence with diluted hydrochloric acid and water, and dried over anhydrous magnesium sulfate. Low-boiling fractions were distilled off under reduced pressure and the residue was purified by silica gel column chromatography (eluent: acetone-n-hexane, 4:6 by volume) to give 1.6 g of pregna-1,4,11(12)-triene-3,20-dione as crystals. The physical properties for the obtained crystal were as follows:
Melting point: 167°–169° C.
NMR spectrum (90 MHz) $\delta_{HMS}^{CDCl_3}$: 0.74, 1.17, 2.15 (each s, each 3H); 5.66 (d, 1H); 6.07–6.40 (m, 3H); 7.12 (d, 1H).

What is claimed is:
1. A pregnane derivative having the general formula

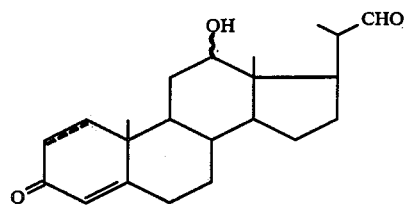

wherein the dotted line --- indicates the possibility of there being a double bond and the wavy line ∿ indicates that the hydroxyl group in either in the α- or in the β-configuration.

2. The pregnane derivative of claim 1, wherein said derivative is 12α-hydroxypregna-1,4-dien-3-one-20-carbaldehyde of the formula

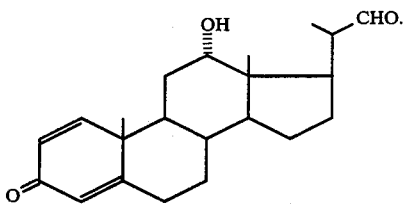

3. The pregnane derivative of claim 1, wherein said derivative is 12β-hydroxypregna-1,4-dien-3-one-20-carbaldehyde of the formula

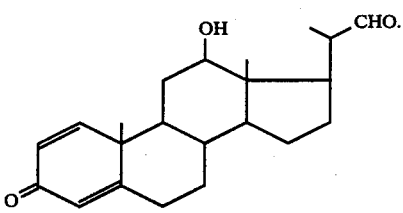

4. The pregnane derivative of claim 1, wherein said derivative is 12α-hydroxypregna-4-en-3-one-20-carbaldehyde of the formula

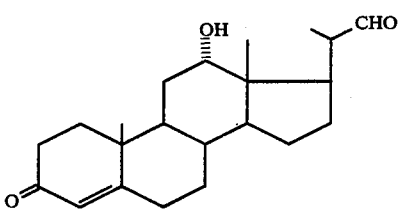

* * * * *